(12) United States Patent
Kouassi

(10) Patent No.: US 10,165,772 B2
(45) Date of Patent: Jan. 1, 2019

(54) METHODS AND COMPOUNDS FOR INCREASING RED BLOOD CELL SURVIVAL

(76) Inventor: Édouard Kouassi, Montreal (CA)

(*) Notice: Subject to any disclaimer, the term of this patent is extended or adjusted under 35 U.S.C. 154(b) by 899 days.

(21) Appl. No.: 13/059,699

(22) PCT Filed: Aug. 21, 2009

(86) PCT No.: PCT/CA2009/001164
§ 371 (c)(1),
(2), (4) Date: Feb. 18, 2011

(87) PCT Pub. No.: WO2010/020052
PCT Pub. Date: Feb. 25, 2010

(65) Prior Publication Data
US 2011/0151428 A1   Jun. 23, 2011

Related U.S. Application Data

(60) Provisional application No. 61/090,727, filed on Aug. 21, 2008.

(51) Int. Cl.
*A01N 1/02* (2006.01)

(52) U.S. Cl.
CPC .................... *A01N 1/0226* (2013.01)

(58) Field of Classification Search
None
See application file for complete search history.

(56) References Cited

U.S. PATENT DOCUMENTS

| | | | |
|---|---|---|---|
| 4,173,626 A * | 11/1979 | Dempski et al. | 424/462 |
| 4,609,372 A | 9/1986 | Carmen et al. | |
| 4,988,691 A * | 1/1991 | Benelli et al. | 514/214.03 |
| 5,387,202 A * | 2/1995 | Baron | 604/300 |
| 5,591,713 A * | 1/1997 | Igari et al. | 424/85.2 |
| 5,858,643 A | 1/1999 | Ben-Hur et al. | |
| 6,150,085 A | 11/2000 | Hess et al. | |
| 7,220,747 B2 | 5/2007 | Dumont et al. | |

FOREIGN PATENT DOCUMENTS

| | | |
|---|---|---|
| EP | 0799026 | 4/2000 |
| WO | WO 00/74649 A2 * | 12/2000 |
| WO | PCT/CA09/001164 | 8/2009 |

OTHER PUBLICATIONS

Anderson et al. "The Composition of Normal Rat Blood". Journal of Biological Chemistry. 1930; 86(1):157-160.*
Heyssel RM. "Determination of Human Platelet Survival Utilizing C14-Labeled Serotonin". J Clin Invest. 1961. 40(12); 2134-2142.*
Wymenga et al. "Effects of Peripheral Stem Cell or Bone Marrow Reinfusion on Peripheral Serotonin Metabolism". Bone Marrow Transplantation. 1999; 24:1015-1018.*
Li et al. "Effects of Serotonin on Platelet Activation in Whole Blood". Blood Coagul Fibrinolysis. Nov. 1997; 8(8):517-523. Abstract.*
Tesoriere et al. "Melatonin Protects Human Red Blood Cells from Oxidative Hemolysis: New Insights into the Radical Scavenging Activity". J Pineal Res. Sep. 1999; 27(2):95-105. (Year: 1999).*
Kriebardis et al. "Progressive Oxidation of Cytoskeletal Proteins and Accumulation of Denatured Hemoglobin in Stored Red Cells". J Cell Mol Med. 2007; 11(1):148-155. (Year: 2007).*
Gribble, Gordon W., "Recent developments in indole ring synthesis—methodology and applications", J. Chem Soc., Perkin Trans. 1, 2000, 1045-1075.
Cacchi et al., "Synthesis of functionalization of indoles through palladium-catalyzed reactions", Chem Rev., 2005, 105:2873-2920.
Humphrey et al., "Practical methodologies for the synthesis of indoles", Chem. Rev. 2006, 106:2875-2911.
Clinical Practice of Transfusion Medicine, 3rd edition, Lawrence D. Petz (Editor), Steven Kleinman (Editor), Scott N. Swisher (Editor), Richard K. Spence (Editor), Ronald G. Strauss (Editor), Churchill-Livingston publishers, N.Y., 1996.
Blood Banking and Transfusion Medicine: Basic Principles and Practice, 2nd edition, by Christopher D. Hillyer MD, Leslie E. Silberstein MD, Paul M. Ness MD, Kenneth C. Anderson MD, John D. Roback, Churchill Livingstone, 2006.
Butkerait et al., "Expression of the human 5-hydroxytryptamine 1a receptor in Sf9 cells", The Journal of Biochemistry, 270:18691-18699, 1995.

* cited by examiner

Primary Examiner — Leslie A. Royds Draper
(74) Attorney, Agent, or Firm — Alain Dumont

(57) ABSTRACT

Methods and compositions for increasing red blood cell survival and/or inhibiting hemolysis using indole-comprising compounds are described. Such methods and compositions may be useful for blood and blood product storage and preservation applications.

6 Claims, 14 Drawing Sheets

D. Day 14    E. Day 21

F.

A. Day 0

(-) 5-HT (+) 5-HT (100 μM)

Normochromic RBCs

B. Day 7

(-) 5-HT

Hypochromic RBCs with cytoplasmic inclusions (Heinz bodies)

(+) 5-HT (100 μM)

Normochromic RBCs

C. Day 91, 4°C

(−) 5-HT  (+) 5-HT (100 µM)

A. 37°C

B. Room temperature (21 – 23°C)

A

B

D. Day 5

0 µM 5-HT     1 µM 5-HT     10 µM 5-HT     100 µM 5-HT

E. Day 7

0 µM 5-HT     1 µM 5-HT     10 µM 5-HT     100 µM 5-HT

METHODS AND COMPOUNDS FOR INCREASING RED BLOOD CELL SURVIVAL

CROSS REFERENCE TO RELATED APPLICATIONS

This application is a National Entry Application of PCT application no PCT/CA2009/001164 filed on Aug. 21, 2009 and published in English under PCT Article 21(2), which itself claims the benefits of U.S. provisional application serial No. 61/090,727, filed on Aug. 21, 2008. All documents above are incorporated herein by reference in their entirety.

TECHNICAL FIELD

The present invention relates to the field of blood and blood product storage and more particularly to compositions and methods for increasing red blood cell survival and improving blood preservation.

BACKGROUND ART

Red blood cells (erythrocytes) are perhaps the most recognizable component of whole blood. Red blood cells contain hemoglobin, a complex iron-containing protein that carries oxygen throughout the body while giving blood its red color. The percentage of blood volume composed of red blood cells is called the "hematocrit".

The ability to store and preserve red blood cells (RBCs) for later re-infusion into patients is a relatively recent technological development that was the harbinger to modern surgical practice. Such preservation is scientifically tricky and the steps to achieving longer storage duration and higher quality re-infused red blood cells have been incremental. As soon as they are collected from a donor, red blood cells begin to die as they coagulate, starve, lose ATP, 2,3-DPG, membrane surface area and integrity, and hemoglobin (Hb). Acid-citrate-dextrose (ACD), comprising citrate as an anticoagulant and dextrose as the sole nutrient utilized by red blood cells, and Citrate-phosphate-dextrose solution (CPD), adding phosphate as a metabolic source and for membrane retention, were developed to circumvent this problem. However, whole blood cells kept in CPD and ACD were limited to storage of 21 days.

Almost all of the whole blood collected now is made into components, and the RBC fraction is stored as packed RBCs. For blood drawn into the conservation solution systems, RBCs are packed by centrifugation, plasma is removed so that RBCs make up 80% of the volume, and then conservation solution is added sterilely.

Despite these advances, the concern has been steadily growing over both the national, and worldwide blood supplies. Both the integrity and reliability of existing supplies, and the ability to build larger stocks over time, has been brought into question. One reason for this is the relatively short period of storage stability of blood products. Currently, packed RBCs (red blood cell concentrates, or RCC), the dominant form of blood product for transfusions and the like, are limited to a 42-day storage period.

The gold standard for red cell viability is the survival of 75% of injected radiolabelled cells at 24 h—an arbitrary standard that permits a quarter of transfused erythrocytes to be non-viable. Time-dependent changes in RBC quality and quantity are commonly referred to as the storage lesion. In storage, adenosine triphosphate (ATP) declines with time, resulting in changes in red-cell shape, and decline in membrane lipid content and cell rigidity. Other changes also occur in storage: cells metabolize the glucose in the preservative solution, lactate is produced, pH starts to fall, potassium increases in the suspending medium, free hemoglobin and iron are released from haemolysed red cells, and membrane lipid is shed in the form of vesicles resulting in a diminished function of these cells. Recent evidences suggest that the storage lesion could be responsible for transfusion-associated complications such as immunosuppression and organ failure syndrome.

To circumvent this, compositions were developed to restore volume, nutrients, and other useful RBC stabilizers. These solution compositions for the preservation of red blood cells (RBCs) after their separation from whole blood are intended to be tailored specifically to the needs of RBCs. Example of additive/conservation solution are ACED (citric acid-sodium citrate-dextrose), CPD (citrate-phosphate-dextrose), CPD2, Adsol® (AS-I), Nutricel® (AS-3), Optisol® (AS-5), ErythroSol®, and the like. Typically, these conservations include a carbohydrate, such as glucose or mannitol, at least one phosphate salt, a citrate, and other balancing salts. Red blood cells (RBCs) stored in these solutions, nevertheless, undergo steady deterioration after about 6 weeks as determined by the inability of 75% of such cells to survive in the circulation for 24 hours after re-infusion back into the human donor. It has been observed that during continued refrigerated storage, glucose is consumed at a decreasing rate, as the concentration of metabolic waste, i.e., lactic acid and hydrogen ions, increases. Such a decrease in the rate of glucose metabolism leads to depletion of adenosine triphosphate (ATP), which directly correlates to the recovery of RBCs when the cells are returned to the circulation.

Thus, there is a need for novel RBC storage compositions formulated to improve RBC preservation that results in longer storage duration, reduced storage lesion and/or improved physiological functions of the transfused RBC. Consequently, there remains a need for improved RBC storage compositions and method of manufacture thereof.

The present description refers to a number of documents, the content of which is herein incorporated by reference in their entirety.

SUMMARY OF THE INVENTION

In a first aspect, the present invention provides a composition for decreasing hemolysis in a blood sample or a blood product sample, said composition comprising a compound of formula I:

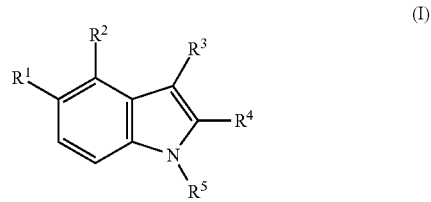

wherein:
$R^1$ is H, OH, $OCH_3$, $OCH_2CH_3$ or $OCOCH_3$;
$R^2$ is H or $OCH_2CH(OH)CH_2NHCH(CH_3)_2$
$R^3$ is H, $CH_2CH_2NHR^6$ or $CH_2COOR^7$;
$R^4$ is H, $CH_3$ or $CH_2CH_3$;
$R^5$ is H or

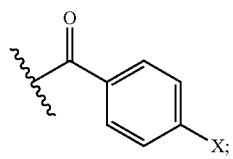

$R^6$ is H or $COCH_3$;
$R^7$ is H, $CH_3$ or $CH_2CH_3$; and
X is Cl, Br, I, F, OH, CN or $NO_2$;
and a physiologically acceptable buffer.

In an embodiment, $R^1$ is OH or $OCH_3$. In an embodiment, $R^7$ is H. In an embodiment, the X is Cl.

In an embodiment, $R^1$ is OH, $R^2$ is H, $R^3$ is $CH_2CH_2NHR^6$, $R^4$ is H, $R^5$ is H, and $R^6$ is H.

In another embodiment, $R^1$ is $OCH_3$, $R^2$ is H, $R^3$ is $CH_2CH_2NHR^6$, $R^4$ is H, $R^5$ is H, and $R^6$ is $COCH_3$.

In another embodiment, $R^1$ is H, $R^2$ is $OCH_2CH(OH)CH_2NHCH(CH_3)_2$, $R^3$ is H, $R^4$ is H, and $R^5$ is H.

In another embodiment, $R^1$ is $OCH_3$, $R^2$ is H, $R^3$ is $CH_2COOR^7$, $R^4$ is $CH_3$, $R^5$ is

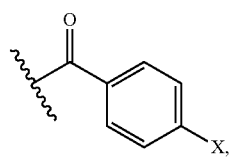

$R^7$ is H and X is Cl.

In another aspect, the present invention provides a method for decreasing hemolysis in a blood sample or a blood product sample comprising contacting said sample with the above-mentioned compound of formula I.

In another aspect, the present invention provides a blood or blood product storage kit comprising (a) a container and (b) the above-mentioned compound of formula I.

In another aspect, the present invention provides a method of preserving or storing red blood cells comprising:
(a) providing red blood cells and a composition for red blood cell preservation, wherein said composition comprises the compound of formula I defined above; and
(b) contacting said red blood cells and said composition such that said red blood cells and said composition form a suspension.

In an embodiment, the above-mentioned physiologically acceptable buffer is an additive solution. In a further embodiment, the above-mentioned additive solution comprises citrate, mannitol, phosphate, dextrose, adenine, sodium chloride, or any combination thereof.

In an embodiment, the above-mentioned blood sample is a whole blood sample.

In another embodiment, the above-mentioned blood product sample is a packed red blood cell sample.

In an embodiment, the above-mentioned composition further comprises an anticoagulant.

In an embodiment, the above-mentioned compound is present in a additive solution comprising citrate, mannitol, phosphate, dextrose, adenine, sodium chloride, or any combination thereof.

In a further embodiment, the above-mentioned additive solution is AS-3 (Nutricel®).

In an embodiment, the above-mentioned blood sample or blood product sample is stored for at least one week.

In an embodiment, the above-mentioned container is a blood collection tube, bag or bottle.

In an embodiment, the above-mentioned storage kit further comprises an anticoagulant.

In an embodiment, the above-mentioned method of preserving or storing red blood cells further comprises: mixing a sample of collected whole blood containing said red blood cells to be preserved with an anticoagulant solution; treating the collected whole blood/anticoagulant solution mixture to deplete the plasma and platelets and concentrate the red blood cells, thereby obtaining said packed red blood cell sample.

In a further embodiment, the above-mentioned method of preserving or storing red blood cells further comprises removing the white blood cells.

In an embodiment, the above-mentioned treatment is a centrifugation.

In a further embodiment, the above-mentioned method of preserving or storing red blood cells further comprises cooling and storing said suspension at a temperature of from about 1° C. to about 6° C.

In another aspect, the present invention provides a red blood cell sample obtained by the above-mentioned method.

In an embodiment, the above-mentioned red blood cell sample is a packed red blood cell sample.

Other objects, advantages and features of the present invention will become more apparent upon reading of the following non-restrictive description of specific embodiments thereof, given by way of example only with reference to the accompanying drawings.

DISCLOSURE OF INVENTION

Figure 1:
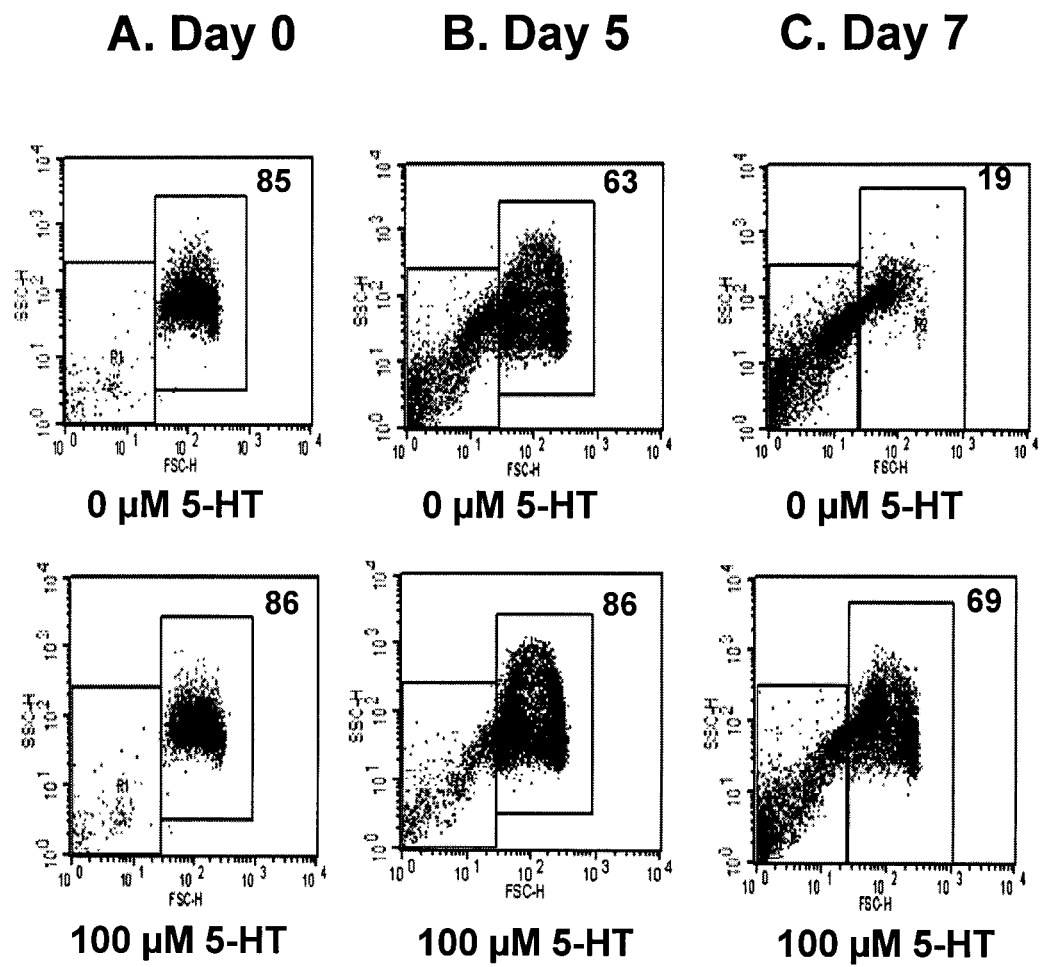
FIG. 1 shows a typical time- and concentration-dependent effects of serotonin (5-HT) on human red blood cell (RBC) survival. RBCs were incubated in vitro at 37° C., and cells were analyzed by flow cytometry for assessment of the relative proportions of dead and viable cells. Forward scatter (FSC)/side scatter (SSC) dot plots of RBCs incubated in the presence or absence of 5-HT (100 μM) are shown in (A) to (E) for the indicated time points. Two main regions of analysis are set, R1 (left box) and R2 (right box), corresponding to dead and viable RBCs, respectively. The proportion of viable cells remaining at each time-point is indicated next to the R2 region (upper right in the dot plots). (F) Typical concentration-dependent effects of 5-HT (0-100 μM) on RBCs incubated for different periods of time.
Figure 1:
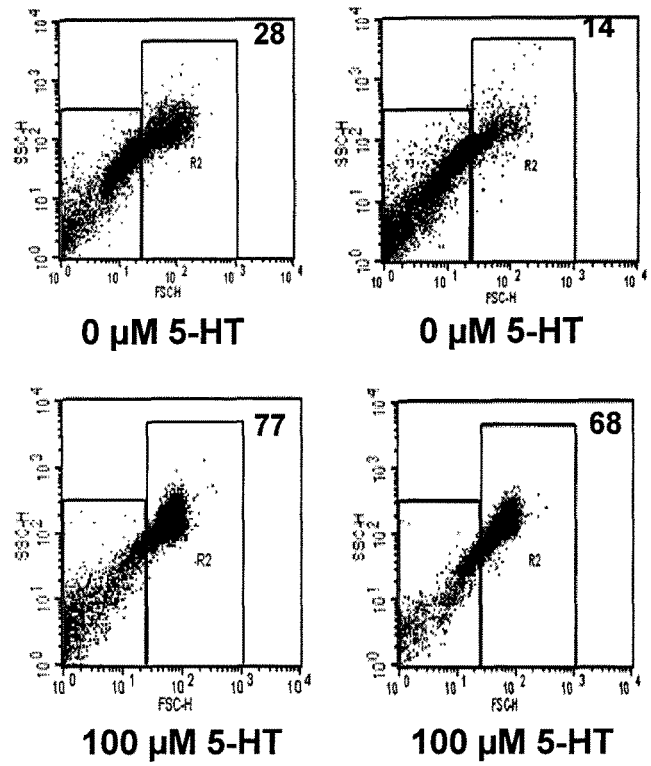
Figure 1:
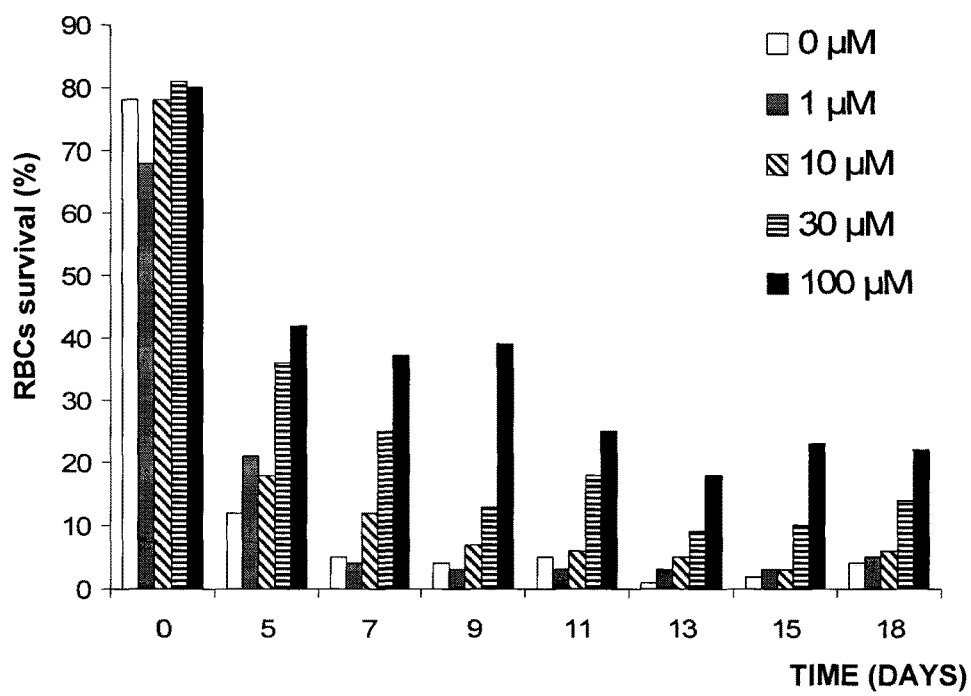

In the studies described herein, the present inventor has demonstrated that human and mouse red blood cells (RBCs) incubated in the presence of serotonin under various conditions show increased survival as compared to RBCs incubated in a serotonin-free medium. He has further demonstrated that other compounds comprising an indole moiety, namely melatonin, pindolol and indomethacin, also protect RBCs. The present invention thus generally relates to compounds, compositions, methods and kits for preventing/decreasing hemolysis, for example in blood preservation and storage applications.

Accordingly, in a first aspect, the present invention provides a composition for increasing the survival of red blood cells (e.g., for decreasing/inhibiting hemolysis), the composition comprising an indole-comprising compound and a physiologically or pharmaceutically acceptable carrier, excipient or diluent (e.g., buffer). Indole-comprising compound as used herein refers to a compound (naturally-occurring or synthetically-produced) comprising an indole moiety.

In an embodiment, the above-mentioned indole-comprising compound is a compound of formula I:

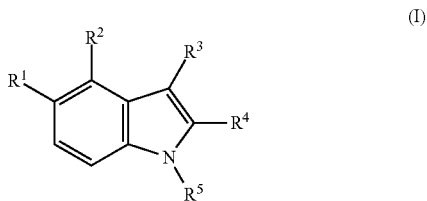

wherein:
$R^1$ is H, OH, $OCH_3$, $OCH_2CH_3$ or $OCOCH_3$;
$R^2$ is H or $OCH_2CH(OH)CH_2NHCH(CH_3)_2$
$R^3$ is H, $CH_2CH_2NHR^6$ or $CH_2COOR^7$;
$R^4$ is H, $CH_3$ or $CH_2CH_3$;
$R^5$ is H or

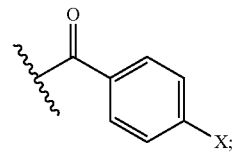

$R^6$ is H or $COCH_3$;
$R^7$ is H, $CH_3$ or $CH_2CH_3$; and
X is Cl, Br, I, F, OH, CN or $NO_2$.

In an embodiment, $R^1$ is OH or $OCH_3$. In another embodiment, $R^7$ is H. In yet another embodiment, X is Cl.

In an embodiment, the above-mentioned indole-comprising compound is a compound of formula I wherein: $R^1$ is OH, $R^2$ is H, $R^3$ is $CH_2CH_2NHR^6$, $R^4$ is H, $R^5$ is H, and $R^6$ is H (serotonin).

In another embodiment, the above-mentioned indole-comprising compound is a compound of formula I wherein: $R^1$ is $OCH_3$, $R^2$ is H, $R^3$ is $CH_2CH_2NHR^6$, $R^4$ is H, $R^5$ is H, and $R^6$ is $COCH_3$ (melatonin).

In another embodiment, the above-mentioned indole-comprising compound is a compound of formula I wherein: $R^1$ is H, $R^2$ is $OCH_2CH(OH)CH_2NHCH(CH_3)_2$, $R^3$ is H, $R^4$ is H, and $R^5$ is H (pindolol).

In another embodiment, the above-mentioned indole-comprising compound is a compound of formula I wherein: $R^1$ is $OCH_3$, $R^2$ is H, $R^3$ is $CH_2COOR^7$, $R^4$ is $CH_3$, $R^5$ is

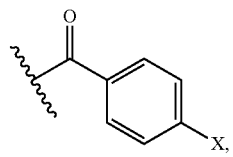

$R^7$ is H and X is Cl (indomethacin).

Methods for synthesizing indole-comprising compounds are well known in the art and include, for example, the Fischer indole synthesis, the Bartoli indole synthesis, the Fukuyama indole synthesis, the Gassman indole synthesis, the Hemetsberger indole synthesis, the Larock indole synthesis, the Madelung indole synthesis, the Nenitzescu indole synthesis, the Reissert indole synthesis and the Baeyer-Emmerling indole synthesis (Gordon W. Gribble, *J. Chem. Soc.*, Perkin Trans. 1, 2000, 1045-1075; Cacchi, S and Fabrizi, G., *Chem Rev.* 2005, 105: 2873-2920; Humphrey, G. R. and Kuethe, J. T., *Chem. Rev.* 2006, 106: 2875-2911.

In another aspect, the present invention provides a composition for increasing red blood cell survival comprising a serotonergic activator and a physiologically- or pharmaceutically-acceptable carrier, excipient or diluent (e.g., buffer). In another aspect, the present invention provides a composition for decreasing hemolysis in a blood sample or a blood product sample, said composition comprising a serotonergic activator and a physiologically acceptable buffer (e.g., an additive/conservation solution). As used herein, "serotonergic activator" refers to an agent which increases a serotonin-mediated biological activity, for example by triggering or activating one or more pathway(s) associated with a serotonin receptor. Such serotonergic activators include, for example, natural and synthetic agonists of serotonin receptors (e.g., 5-HT1A, 5-HT1B, 5-HT2A and/or 5-HT2B) such as serotonin, as well as derivatives, analogs and prodrugs of serotonin. Serotonin receptor agonists are known in the art, and examples of such agonists are described in PCT publications NOs. WO 02/059082, WO 00/012482, WO 00/012482, WO 00/044753, WO 00/12510 and WO 00/12475. In an embodiment, the above-mentioned serotonergic activator is a compound of formula I defined above. In another embodiment, the above-mentioned serotonergic activator is serotonin or an analog thereof.

As used herein, the term "physiologically-acceptable buffer" refers to buffering agents which yield cations and anions either normally found in the blood, plasma, or serum of an animal (e.g., a mammalian such as a human), and that may be tolerated when introduced into an animal. The carrier, excipient or diluent may be any buffer, solution, or composition (e.g., an additive/conservation solution) generally used for blood storage applications, and may comprises for example an anticoagulant. Such composition may be particularly useful in blood and/or blood product storage/preservation applications (e.g., to prevent or minimize red blood cell loss during storage). Accordingly, in another aspect, the present invention provides a composition for increasing/improving the preservation of a blood sample or a blood product sample (e.g., increasing the half-life), said composition comprising an indole-comprising compound and a physiologically-acceptable buffer. In an embodiment, the above-mentioned indole-comprising compound is a compound of formula I defined above.

The present invention also provides a composition for increasing/improving the preservation of a blood sample or a blood product sample (e.g., increasing the half-life), said composition comprising a serotonergic activator and a physiologically-acceptable buffer.

In an embodiment, the above-mentioned physiologically-acceptable buffer is an additive/conservation solution.

As used herein, "blood sample" and "blood product sample" refers to any blood-based or blood-derived sample that comprises red blood cells. Such sample may be transfused directly into a patient or into the circulatory system of a patient in need thereof, for example. Typical blood and blood product sample include but are not limited to: warm or cold blood, stored or fresh blood; treated blood, such as blood diluted with a physiological solution, including but not limited to saline, nutrient, and/or anticoagulant solutions; whole blood; anti-coagulated whole blood (AWB); red blood cell concentrate (RCC); packed red blood cells obtained from AWB; red blood cells separated from plasma and resuspended in physiological fluid; and analogous blood products derived from blood or a blood component or derived from bone marrow. In accordance with the invention, each of these blood samples and blood product samples may be processed using methods well known in the art. In an embodiment, the above-mentioned indole-comprising compound is added before, during or after the purification of the blood product sample (e.g., packed red blood cells, red blood cell concentrate).

As used herein, the term "additive solution" or "conservation solution" is intended to mean a solution designed for blood and blood product storage, so as to preserve blood/blood product integrity and/or prevent blood cell death. Typical additive/conservation solutions include, for example, ACED (citric acid-sodium citrate-dextrose), CPD (citrate-phosphate-dextrose), CPDA (citrate-phosphatedextrose-adenine), Adsol® (AS-I), Nutricel® (AS-3), Optisol® (AS-5), ErythroSol®, CPD2 (CPDA+Adsol®) and the like. Typically, the composition includes a carbohydrate, such as glucose or mannitol, at least one phosphate salt, a citrate, and other balancing salts. In accordance with the present invention, an effective amount of a compound of formula I defined above (e.g., an amount effective for preventing or minimizing red blood cell death or hemolysis during storage) may be added to a conservation solution designed for improving blood storage, which typically includes a carbohydrate, such as glucose or mannitol, at least one phosphate salt, a citrate, and other balancing salts. In an embodiment, the above-mentioned conservation solution comprises citrate, mannitol, phosphate, dextrose, adenine, sodium chloride, or any combination thereof.

The present invention further provides a blood or blood product storage kit/package comprising (a) a container and (b) an indole-comprising compound. In an embodiment, the above-mentioned indole-comprising compound is a compound of formula I defined above.

The present invention further provides a blood or blood product storage kit/package comprising (a) a container and (b) a serotonergic activator.

In an embodiment, the above-mentioned container is a container typically used for blood collection, such as a blood collection (or blood donation/transfusion) bag, tube (e.g., Vacutainer™) or bottle, which are generally known and commercially available.

In embodiments, the kit may further comprise other components useful for collecting blood (e.g., venous blood) from a subject, such as a needle (e.g., hypodermic needle), tubing, sterile gauze, as well as instructions for collecting and/or storing blood. In an embodiment, the kit/package further comprises a conservation and/or additive solution. In an embodiment, the conservation/additive solution is comprised within the above-mentioned container.

In another aspect, the present invention provides a method for increasing red blood cell survival (or decreasing red blood cell death) comprising contacting said red blood cell with an indole-comprising compound. In an embodiment, the above-mentioned indole-comprising compound is a compound of formula I defined above.

In another aspect, the present invention provides a method for increasing red blood cell survival (or decreasing red blood cell death) comprising contacting said red blood cell with a serotonergic activator.

In another aspect, the present invention provides a method of increasing the preservation of a blood sample or a blood product sample (e.g., by reducing red blood cell death or hemolysis) comprising contacting said sample with an indole-comprising compound. In an embodiment, the above-mentioned indole-comprising compound is a compound of formula I defined above.

In another aspect, the present invention provides a method of increasing the preservation of a blood sample or a blood product sample (e.g., by reducing red blood cell death or hemolysis) comprising contacting said sample with a serotonergic activator.

In another aspect, the present invention provides a method of preserving whole blood cells for a storage period. The method comprises: (a) mixing a sample of collected whole blood containing RBCs to be stored and plasma with the above-mentioned indole-comprising compound or composition. In an embodiment, the above-mentioned indole-comprising compound is a compound of formula I defined above.

In another aspect, the present invention provides a method of preserving whole blood cells for a storage period. The method comprises: (a) mixing a sample of collected whole blood containing RBCs to be stored and plasma with the above-mentioned serotonergic activator or composition.

In an embodiment, the above-mentioned method of preserving or storing red blood cells further comprises: mixing a sample of collected whole blood containing said red blood cells to be preserved with an anticoagulant solution; treating the collected whole blood/anticoagulant solution mixture to deplete the plasma and platelets and concentrate the red blood cells, thereby obtaining said packed red blood cell sample.

In a further embodiment, the above-mentioned method of preserving or storing red blood cells further comprises removing the white blood cells.

In an embodiment, the above-mentioned treatment is a centrifugation.

RBCs useful in the present invention are those which have been prepared using standard procedures well known in the art (see, for example, *Clinical Practice of Transfusion Medicine*, $3^{rd}$ edition, Lawrence D. Petz (Editor), Steven Kleinman (Editor), Scott N. Swisher (Editor), Richard K. Spence (Editor), Ronald G. Strauss (Editor), Churchill-Livingston publishers, N.Y., 1996; and *Blood Banking and Transfusion Medicine: Basic Principles and Practice,* $2n^d$ edition, by Christopher D. Hillyer M D, Leslie E. Silberstein M D, Paul M. Ness M D, Kenneth C. Anderson M D, John D. Roback, Churchill Livingstone, 2006).

For example, RBCs are separated from their plasma and resuspended in an anticoagulant solution in the normal course of component manufacture. Briefly stated, a standard whole blood sample (about 450 ml±45 ml) containing RBCs and plasma is mixed with an anticoagulation solution to form a suspension of whole blood. The whole blood suspension is thereafter centrifuged to separate the RBCs from the blood plasma thereby forming a packed RBCs. In an embodiment, the process further comprises white blood cell (leukocyte) depletion/reduction using techniques well known in the art. Suitable anticoagulants include conventional anticoagulants known for storage of RBCs. In an embodiment, the anticoagulants include citrate anticoagulants having a pH of 5.5 to 8.0, such as CPD, half-strength CPD and the like.

In accordance with the method of the invention, the above-mentioned composition is added to the packed RBC suspension in an amount sufficient to provide a therapeutic effective amount of recoverable RBCs in the cell suspension. In an embodiment, the composition is added at a volume ranging from about 140 ml to about 400 ml, in a further embodiment from about 180 to about 300 ml.

The RBC suspension is then generally stored in standard polyvinyl chloride (PVC) blood storage bags using either the collection bag or PVC transfer packs of different sizes depending on the volume of the stored aliquot. The RBC suspension is stored at about 1° C. to about 6° C. according to standard blood bank procedures, as described in *Clinical Practice of Transfusion Medicine,* $3r^d$ edition, Lawrence D. Petz (Editor), Steven Kleinman (Editor), Scott N. Swisher (Editor), Richard K. Spence (Editor), Ronald G. Strauss (Editor), Churchill-Livingston publishers, N.Y., 1996.

In an embodiment, the above-mentioned composition also comprises an anticoagulant. Anticoagulants are well known in the art and include, for example, vitamin K antagonists, heparin and derivatives thereof, Factor Xa inhibitors, thrombin inhibitors, and calcium chelating agents (e.g., EDTA, citrate, oxalate).

In an embodiment, the above-mentioned composition, method, and kit are used for the prolonged or long-term storage of a blood sample or a blood product sample. In a further embodiment, the above-mentioned storage is for at least one week. In further embodiments, the above-mentioned storage is for at least two, three, four, five or six weeks.

In another embodiment, the above-mentioned storage is at a temperature from about 1° C. to about 10° C. In a further embodiment, the above-mentioned storage is at a temperature of about 1° C. to about 6° C. In a further embodiment, the above-mentioned storage is at a temperature of about 4° C. In another embodiment, the above-mentioned storage is at room temperature, in an embodiment at a temperature from about 20° C. to about 25° C., e.g., from about 21 to 23° C.

In an embodiment, the above-mentioned indole-comprising compound or serotonergic activator is used or is present at an hemolysis-inhibiting concentration. In an embodiment, the above-mentioned indole-comprising compound serotonergic activator is used or is present at a concentration of at least about 10 μM. In an embodiment, the above-mentioned indole-comprising compound serotonergic activator is used or is present at a concentration of from about 10 μM to about 200 µM. In an embodiment, the above-mentioned indole-comprising compound serotonergic activator is used or is present at a concentration of from about 30 µM to about 150 µM. In a further embodiment, the above-mentioned indole comprising compound serotonergic activator is used or is present at a concentration of at least about 100 µM.

In an embodiment, the above-mentioned RBCs, blood sample or blood product sample are of mammalian origin, in a further embodiment of human origin. The compositions, methods, and kits of the present invention may thus be used for human and veterinary applications.

The following examples are illustrative of various aspects of the invention, and do not limit the broad aspects of the invention as disclosed herein

MODE(S) FOR CARRYING OUT THE INVENTION

The present invention is illustrated in further details by the following non-limiting examples.

Example 1

Materials and Methods

Red blood cells isolation. Venous blood was drawn from healthy volunteers, and RBCs were isolated by centrifugation at 800 rpm to remove platelet-rich plasma, and white blood cells. The resulting pellet of RBCs was washed three times in NaCl 0.9% by centrifugation at 3000 rpm. RBCs were incubated at 37° C., 5% $CO_2$ in 24-well microplates at a concentration of $1x10^6$ cells/ml in RPMI 1640 medium without phenol red containing HEPES/NaOH (pH 7.4) and penicillin (100 U/ml)/streptomycin (100 pg/ml).

Cell culture. Drugs [serotonin (Catalog No. H9525), melatonin (Catalog No. M5250), pindolol (Catalog No. P0778) and indomethacin (Catalog No. 18280)] were all purchased from Sigma-Aldrich. They were added at the indicated concentrations at the beginning of cell incubation (Day 0). Cells were harvested at specific time-points and analyzed by flow cytometry (FACScan™, Becton Dickinson) according to forward and side scatters (FSC and SSC, respectively). FSC is proportional to cell size, while SSC is proportional to cell complexity, which may reflect hemoglobin content of RBCs. The relative proportions of viable and dead RBCs were calculated by setting appropriate regions on the dot plots. In some experiments, RBCs were sorted according to FSC and SSC. Cell density was checked routinely by inverted light microscopy, and cell morphology was assessed by May Grünwald-Giemsa staining followed by light microscopy.

Analysis of serotonin transporter and receptor expression. For Western Blotting of the serotonin transporter and of selected serotonin receptors, total proteins were extracted from freshly isolated RBCs, separated on a 10% acrylamide gel, and transferred on polyvinylidene fluoride (PVDF) membranes. The membranes were incubated overnight at 4° C. with the primary antibody specific for the molecule of interest. After washings, the membrane was incubated at room temperature for 2 hours with appropriate secondary antibody conjugated to HRP, and the presence of specific bands was detected by chemiluminescence. The following polyclonal primary and secondary antibodies were obtained from Santa Cruz: goat anti-5-HTT (Catalog No. sc-1458), goat anti-5-HT1A (Catalog No. sc-32550), goat anti-5-HT1B (Catalog No. sc-1460), goat anti-5-HT2A (Catalog No. sc-15073), goat anti-5-HT2B (Catalog No. sc-15076), HRP donkey anti-goat Ig (Catalog No. sc-2020), and HRP goat anti-rabbit Ig (Catalog No. sc-2004). Detection of beta-actin with mouse monoclonal anti-beta actin primary antibody (mABcam 8226, Abcam) and HRP goat anti-mouse Ig secondary antibody (BD Biosciences) was used as loading control. All the primary antibodies used react with both human and mouse, among other species. Protein extracts from mouse brain were used as positive controls for 5-HTT and all 5-HT receptors. Protein extracts from polymorphonuclear cells (PMN) were used as negative control for the serotonin receptor 5-HT1A. To verify the specificity of the bands detected by Western Blotting, competition studies were performed with blocking peptides ("peptide blockers"). Briefly, protein extracts from human RBCs or from mouse brain were separated on acrylamide gel as described above, and transferred onto PVDF membranes. The membranes were then incubated overnight with the antibody specific for the molecule of interest, in the presence or absence of the corresponding blocking peptide. The following blocking peptides were obtained from Santa Cruz: 5-HTT (Catalog No. sc-1458 P), 5-HT1A (Catalog No. sc-32550 P), 5-HT1B (Catalog No. sc-1460 P), 5-HT2A (Catalog No. sc-15073 P), 5-HT2B (Catalog No. sc-15076 P). These peptides are identical to those injected in animals to generate the specific antibodies against 5-HTT or 5-HT receptors described above. The ratio of the intensity of each band detected by the antibody against 5-HTT or 5-HT receptors to the band detected by anti-actin antibody was calculated. Specificity of the signal(s) detected by Western Blotting was indicated by a decrease in the target molecule/actin ratio in the presence of the blocking peptide, as compared to the ratio in the absence of the blocking peptide.

Example 2

Effect of Serotonin on Human RBC Survival

Flow cytometry analysis of RBCs indicated two main regions according to FSC/SSC cytograms (FIGS. 1A-1E). Cells in region 1 (R1) displayed lower FSC/SSC values, while those in region 2 (R2) had higher FSC/SSC. The proportions of cells in R2 decreased with time of incubation, while those in R1 increased, indicating that RBCs in R1 and R2 were dead and viable cells, respectively. As shown in FIG. 1A, viable RBCs represented 85% of freshly isolated RBCs at day 0. In the absence of 5-HT, this percentage decreased dramatically with time of incubation, with only 14% of viable cells remaining at day 21 (FIG. 1E). In the presence of serotonin (5-HT), the percentage of viable RBCs was higher as compared to controls without 5-HT at all time-points. The effect was particularly pronounced after long incubation times, with 68% of viable cells after 21 days, as compared to 14% in the control, as noted above (FIG. 1E). FIG. 1F shows that optimal effect is observed with 100 µM of 5-HT. Similar dose- and time-dependent increasing effects of 5-HT on RBC viability were observed in three different experiments with RBCs from different donors.

Figure 2:
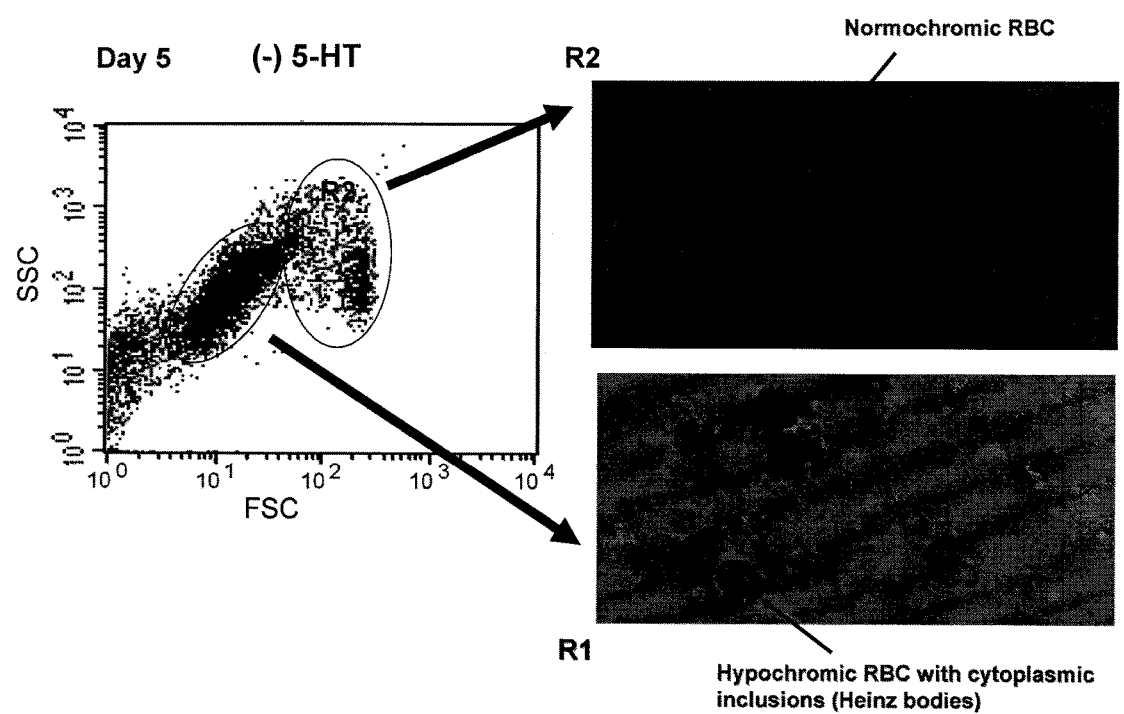
FIG. 2 shows the morphology of viable and dead human RBCs. Cells were incubated in the absence of 5-HT for 5 days, and cell sorting was performed by flow cytometry according to FSC and SSC characteristics. Cells with high FSC/SSC were normochromic (region R2), while cells with lower FSC/SSC were hypochromic, and they displayed cytoplasmic inclusions (region R1), as revealed by May Grünwald-Giemsa staining and light microscopy evaluation.
Figure 3:
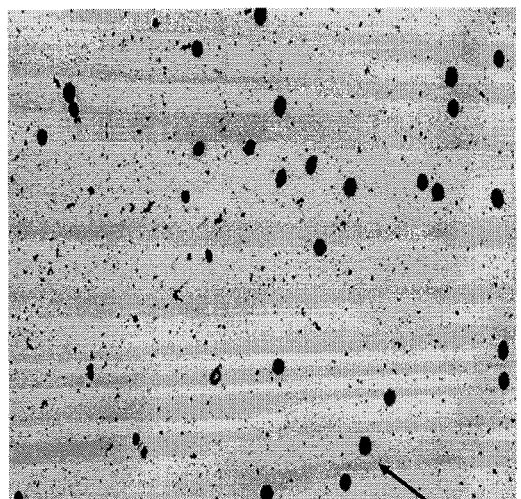
FIG. 3 shows the effects of 5-HT on human RBC quantity and quality at day 0 (A) and day 7 (B) of in vitro incubation at 37° C., and at day 91 of in vitro incubation at 4° C. (C). Cells were incubated in the presence or absence of 5-HT. The density of RBC suspension and their morphology were assessed by May Grünwald-Giemsa staining.
Figure 3:
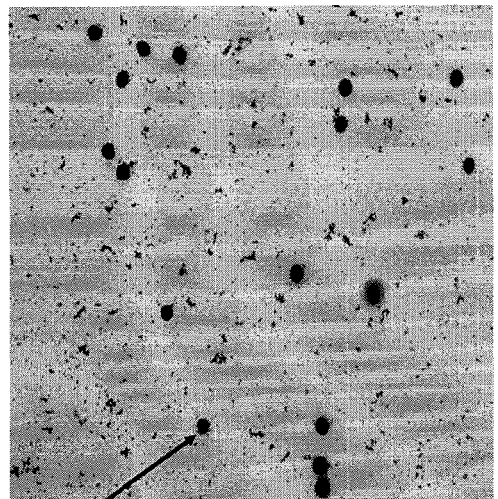
Figure 3:
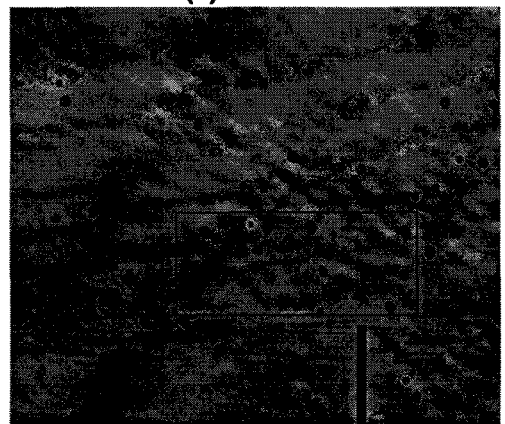
Figure 3:
Figure 3:
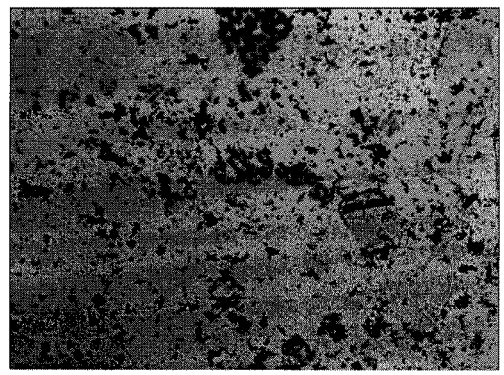
Figure 3:
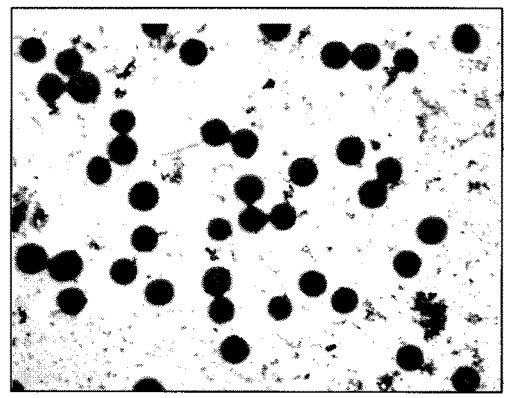

To evaluate the morphology of the two populations of RBCs, these cells were sorted by flow cytometry according to their FSC/SSC characteristics, and stained by the May Grünwald-Giemsa method. As illustrated in FIG. 2, after 5 days of incubation, RBCs with high FSC/SSC (region R2 of the cytogram) were normochromic (FIG. 2, upper right panel), while those with lower FSC/SSC (region R1) were hypochromic with characteristic cytoplasmic inclusions comparable to oxidized hemoglobin (so-called Heinz bodies) (FIG. 2, lower right panel). Cells with intermediate amounts of hemoglobin (between normochromic and hypochromic) were also present in the R2 region (FIG. 2, upper right panel). These results clearly show loss and degradation of hemoglobin upon in vitro incubation of RBCs for several days. At day 0, almost all RBCs were normochromic, and relative cell numbers were comparable in the presence or absence of 5-HT (FIG. 3A). At day 7, in the absence of 5-HT, fewer cells were present, and the majority of these cells were hypochromic with cytoplasmic inclusions (FIG. 3B, left panels). In marked contrast, in the presence of 5-HT, a greater number of cells remained at day 7, as judged by cell density, and the majority of these cells were normochromic (FIG. 3B, right panels). FIG. 3C shows that normochromic red blood cells are observed in RBCs cultured for 91 days at 4° C. in the presence of 5-HT (right panel), but not in RBCs cultured in the absence of 5-HT (left panel).

Example 3

Effect of Serotonin on Human RBC Survival at Different Temperatures

Figure 4:
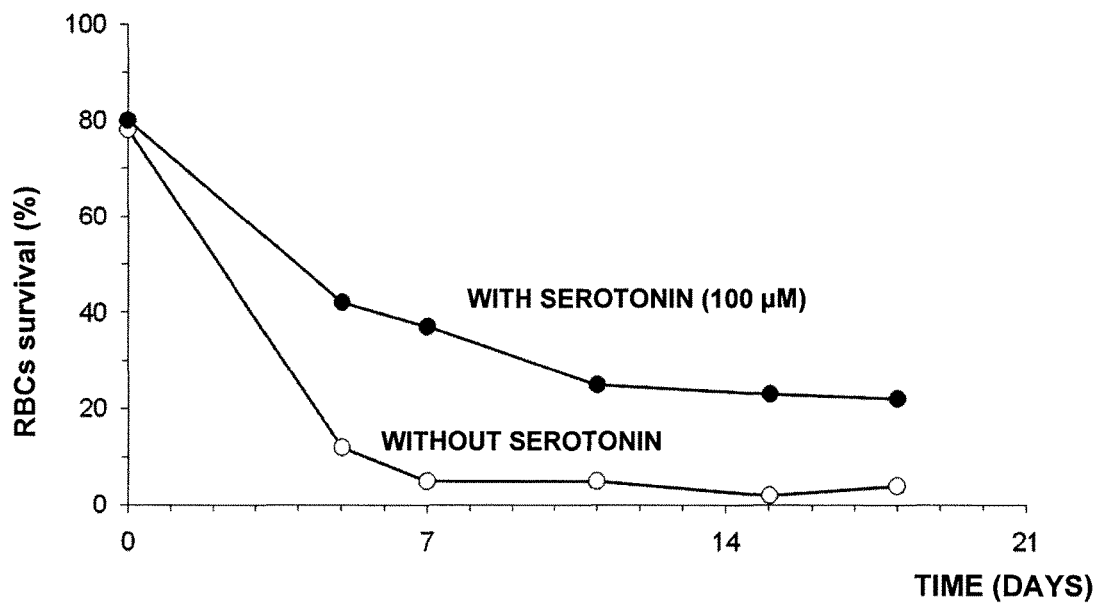
FIG. 4 shows the effects of 5-HT on human RBCs survival at different temperatures of incubation. RBCs were incubated for various lengths of time in the RPMI 1640 medium at 37° C. (A), at room temperature (21 to 23° C.) (B), or at 4° C. (C). 5-HT (100 μM, black circles) or vehicle control (white circles) was added before incubation at Day 0, and cell viability was assessed by flow cytometry at several times as indicated.
Figure 4:
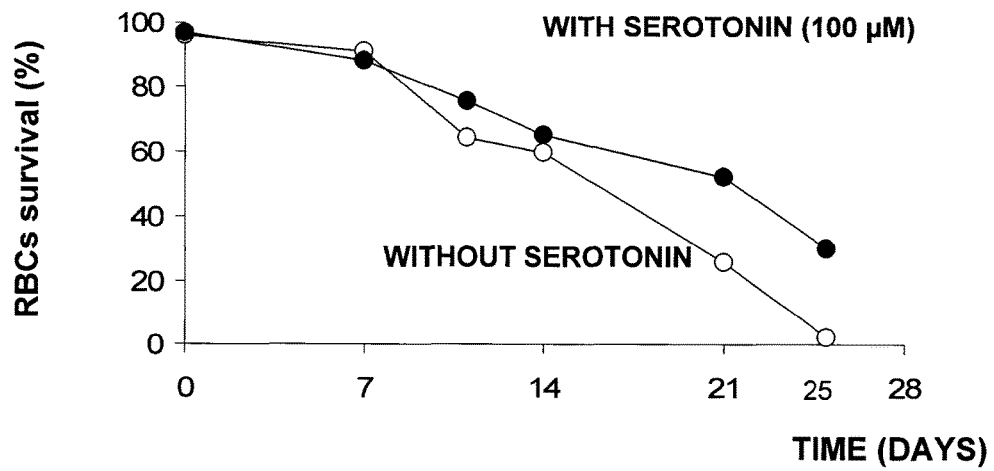
Figure 4:
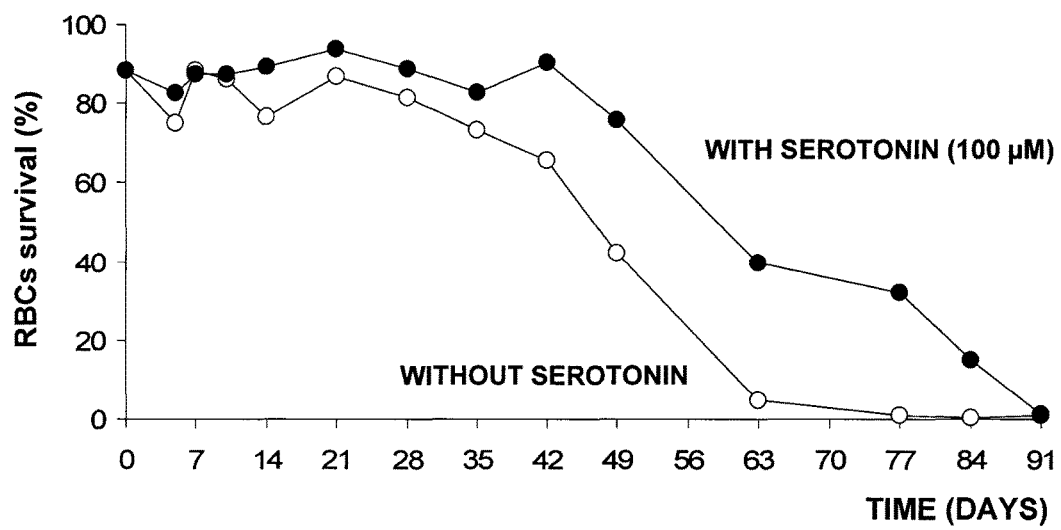
Figure 5:
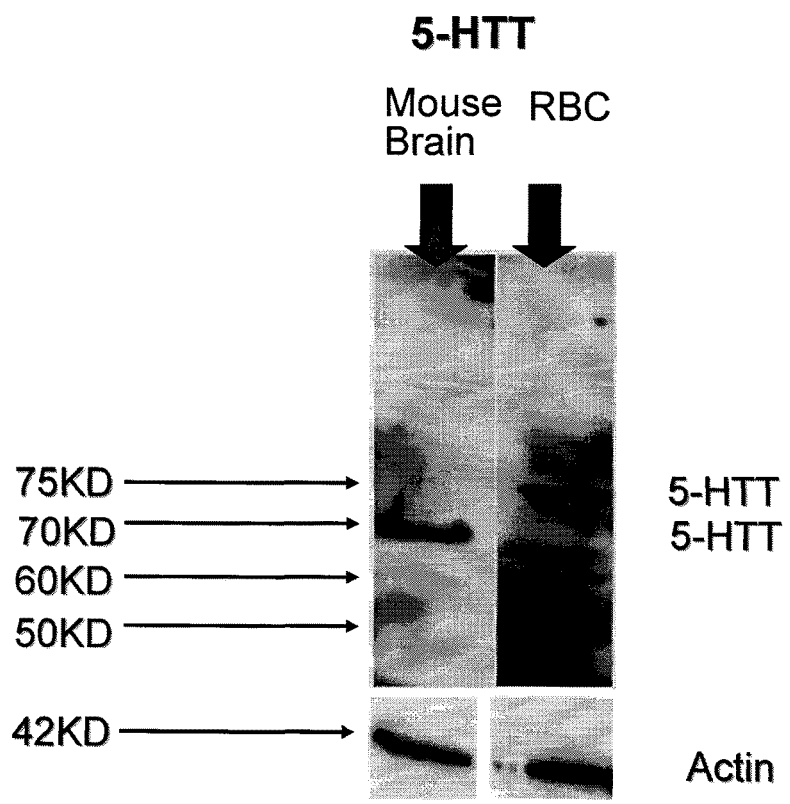
FIG. 5 shows a Western Blotting analysis of serotonin transporter (5-HTT) expression in total protein extracts from human RBCs. Protein extracts from mouse brain were used as positive control. The theoretical molecular weight of 5-HTT is about 70 KDa.
Figure 6:
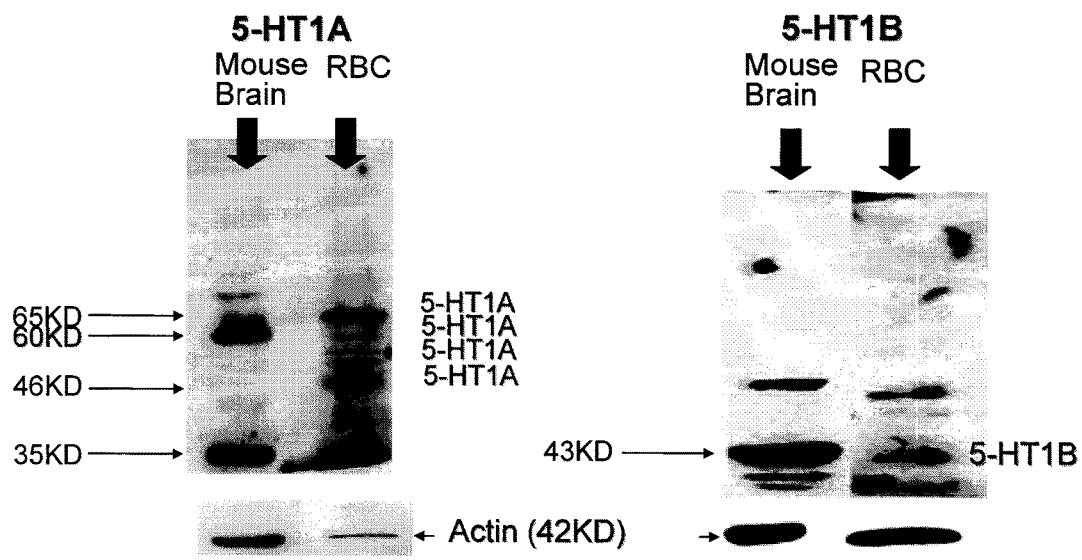
FIG. 6 shows a Western Blotting analysis of the expression of the serotonin receptors 5-HT1A and 5-HT1B in total protein extracts from human RBCs. Protein extracts from mouse brain were used as positive control. The theoretical molecular weights of 5-HT1A and 5-HT1B are 46 KDa and 43 KDa, respectively.
Figure 7:
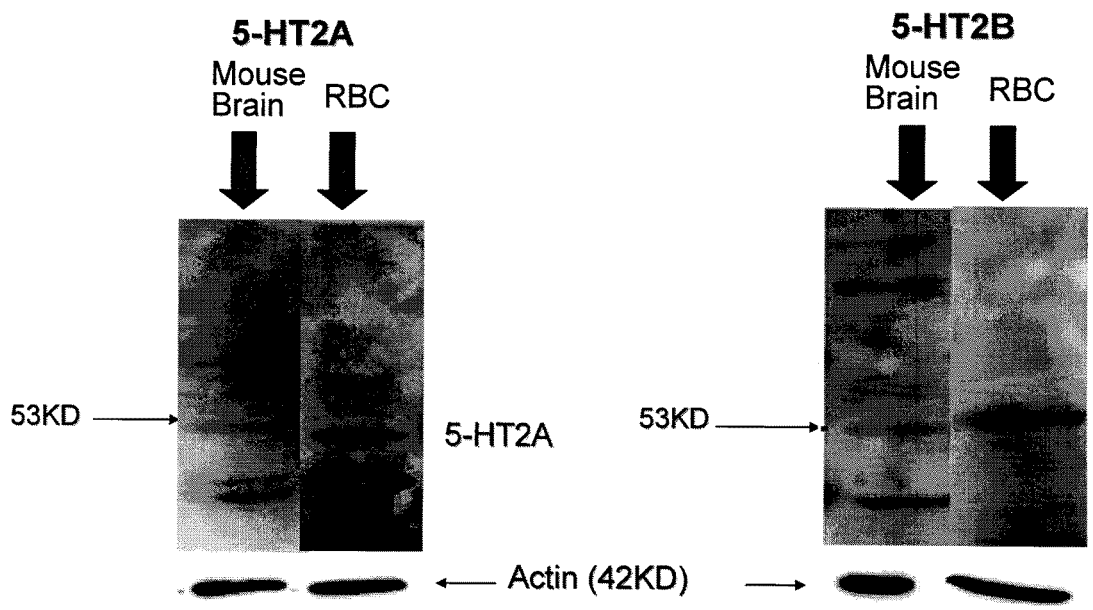
FIG. 7 shows a Western Blotting analysis of the expression of the serotonin receptors 5-HT2A and 5-HT2B in total protein extracts from human RBCs. Protein extracts from mouse brain were used as positive control. The theoretical molecular weight of 5-HT2A and 5-HT2B is 53 KDa.
Figure 8:
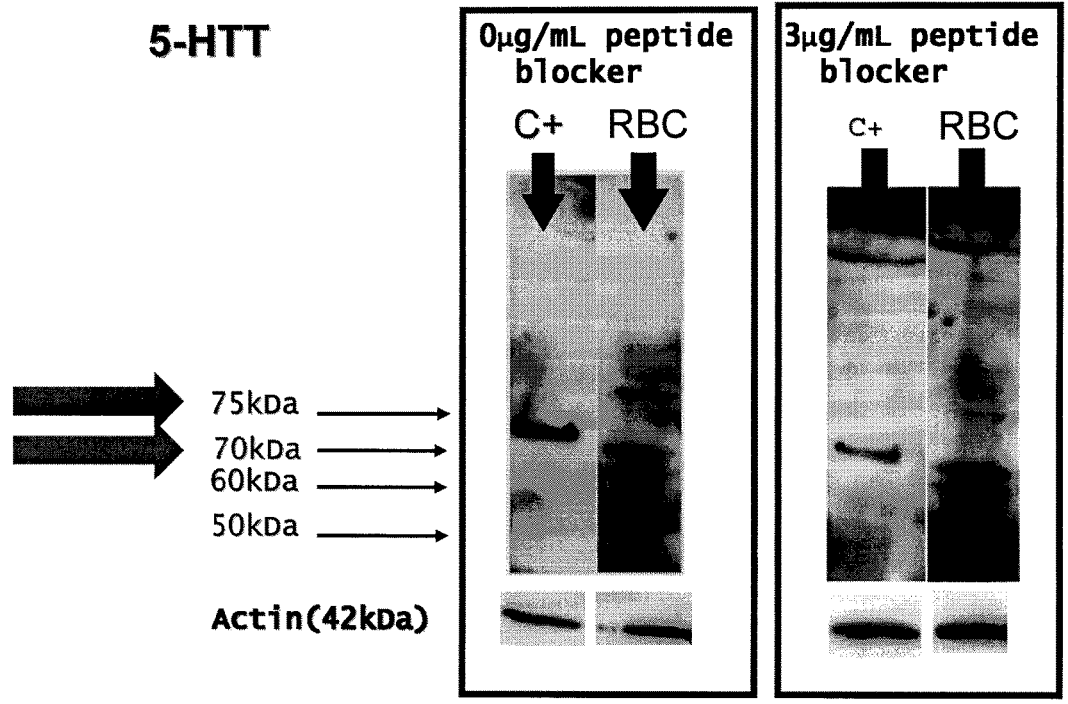
FIG. 8 shows a Western Blotting analysis of serotonin transporter (5-HTT) expression in total protein extracts from human RBCs performed in the presence of a peptide competing with the epitope recognized by the anti-5-HTT antibody (Santa Cruz, Catalog No. sc-1458 P). (A) representative gel showing 5-HTT staining in the absence (left panel) or presence of 3 μg/ml of the peptide blocker; (B) Ratio 5-HTT/Actin calculated in the absence (left bars, light grey) or presence (right bars, dark grey) of the peptide blocker. The symbol "*" indicates that the peptide blocker leads to a reduction of more than 50% in the intensity of the bands revealed by the anti-5-HTT antibody at molecular weights around 70-72 KDa and around 75 KDa, showing specificity of these bands.
Figure 8:
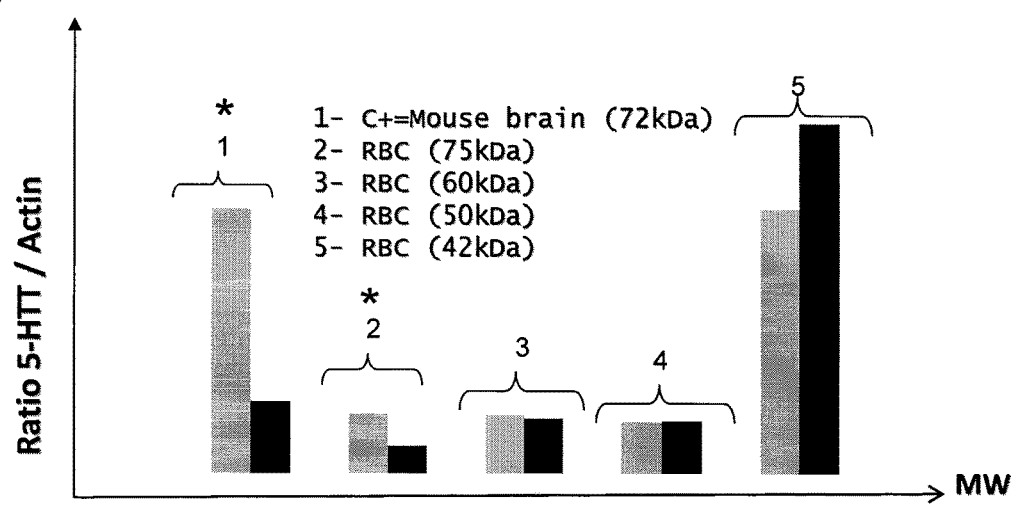
Figure 9:
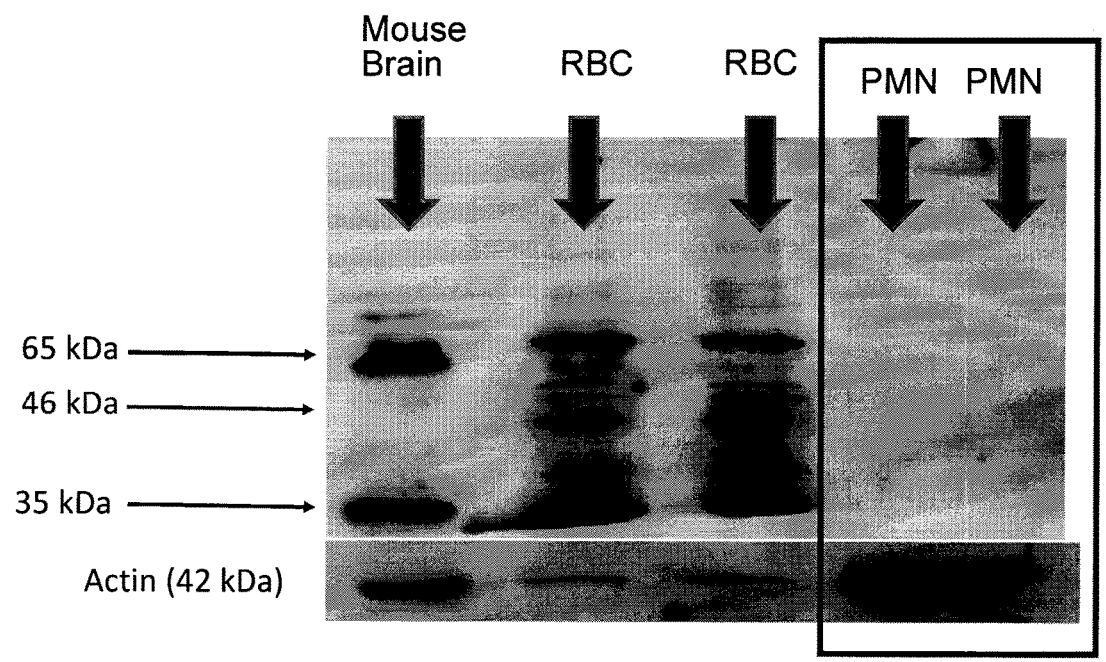
FIG. 9 shows a Western Blotting analysis of the expression of the serotonin receptor 5-HT1A in total protein extracts from human RBCs. Protein extracts from mouse brain and polymorphonuclear cells (PMN) were used as positive and negative controls, respectively.

The capacity of serotonin to increase survival of RBCs incubated at various temperatures was tested. The results presented at FIG. 4A-C show that the protecting effect of serotonin on RBCs is observed at different temperatures (37° C., room temperature (21-23° C.) as well as 4° C.).

Example 4

Expression of the Serotonin Transporter and Serotonin Receptors by RBCs

Figure 10:
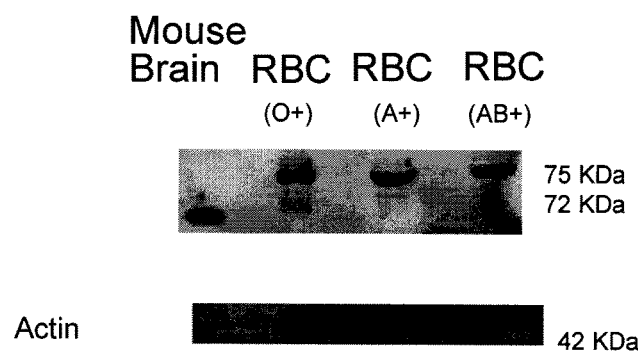
FIG. 10 shows Western Blotting analysis of serotonin transporter (5-HTT) in membrane extracts of human RBCs from three different subjects of blood groups $O^+$, $A^+$ and $AB^+$.

The expression of the 5-HT transporter (5-HTT) and specific 5-HT receptors (5-HT1A, 5-HT1B, 5HT2A and 5HT2B) by RBCs was determined by Western Blotting on total protein extracts. As shown in FIGS. 5 to 9, 5-HTT, 5-HT1A, 5-HT1B, 5-HT2A and 5-HT2B are all expressed in human RBCs. The fact that several bands with different molecular weights are revealed with antibodies against the 5-HT1A protein (FIG. 6) may be due to post-translational modifications, including different levels of phosphorylation and/or palmitoylation, as previously reported (Butkerait et al., *The Journal of Biological Chemistry* 270: 18691-18699, 1995). FIG. 10 shows that 5-HTT is detected in membrane extracts from RBCs obtained from subjects of different blood groups.

Example 5

Effect of Serotonin on the Survival of RBCs Incubated in AS-3 Solution

Figure 11:
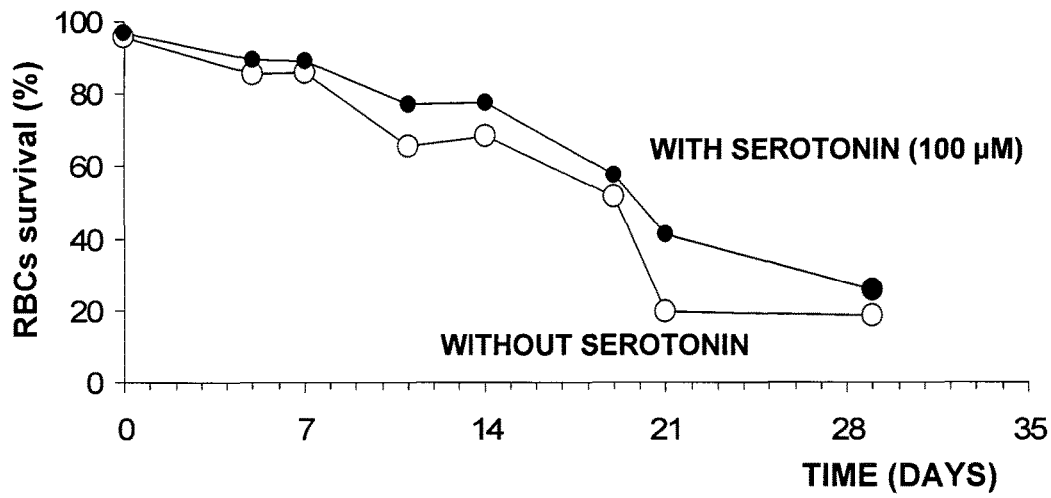
FIG. 11 shows the effect of 5-HT on the survival of human RBCs cultured in AS-3 solution. AS-3 is an additive solution commonly used for storage of RBCs. RBCs were incubated in home-made (A) and commercially available (B) AS-3 solution (Haemonetics, Catalog No. 0460a-00) for various lengths of time at 4° C. in the absence (white circles) or presence (100 μM, black circles) of 5-HT, and cell viability was assessed by flow cytometry at several times as indicated. The home-made AS-3 was prepared in sterile water as follows: Sodium chloride (NaCl, 2.35 g), D-Glucose (Dextrose, 5.5 g), Adenine (0.15 g), Citric Acid (0.21 g), Sodium Phosphate dibasic ($Na_2HPO_4$ anhydrous, 1.380 g) were dissolved in 500 ml of sterile water. The pH of the solution was adjusted at 7.39.
Figure 11:
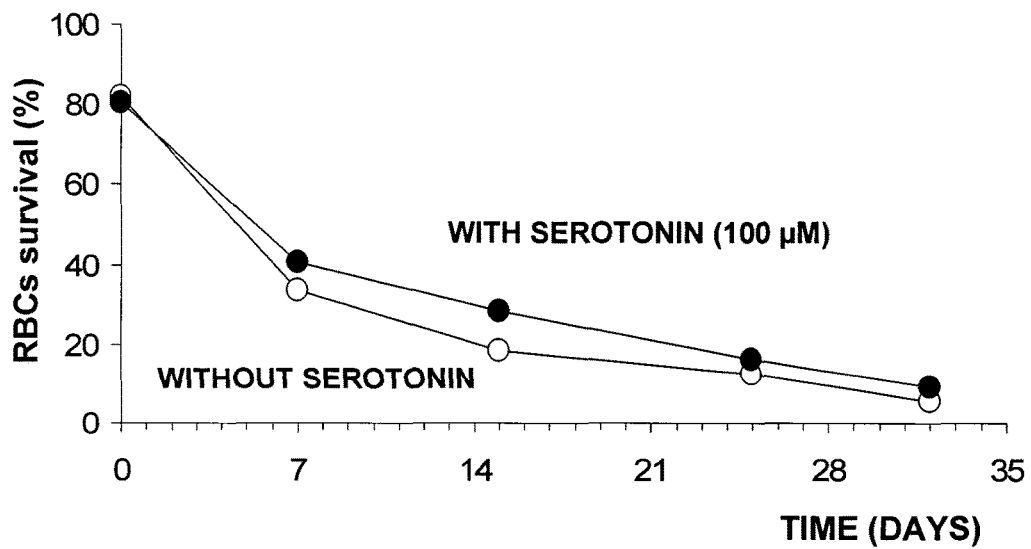

The effect of 5-HT on the survival of human RBCs cultured in AS-3 solution was assessed. AS-3 (sold under the trade name Nutricel®) is an additive solution commonly used for storage of RBCs. FIG. 11 shows that 5-HT also increases the survival of RBCs incubated in home-made (FIG. 11A) or commercially available (FIG. 11B) AS-3 solution.

Example 6

Protecting Effect of 5-HT Against the Toxicity of Fetal Bovine Serum (FBS) on Human RBCs It was next tested whether 5-HT protects human RBCs against the toxicity of fetal bovine serum (FBS). Human RBCs were incubated in the presence or absence of FBS (2%) with increasing concentrations of 5-HT (0, 1, 10 and 100 µM) for time periods varying from day 0 to day 10. Cell viability was analyzed by flow cytometry at day 0, 8 and 10 using RBCs light scatter properties to distinguish dead cells (region R1) and viable cells (region R2). The percentage of viable cells was calculated for each conditions and the results are presented in Table I.

TABLE I

Effect of 5-HT against the toxicity of fetal bovine serum (FBS) on human RBCs

| | % of viable cells (% of cells in the R2 region) | | | | | |
|---|---|---|---|---|---|---|
| | Day 0 | | Day 8 | | Day 10 | |
| Treatment | No FBS | With 2% FBS | No FBS | With 2% FBS | No FBS | With 2% FBS |
| 0 µM 5-HT | 81 | 71 | 18 | 0.60 | 14 | 0.60 |
| 1 µM 5-HT | 85 | 75 | 21 | 0.62 | 16 | 0.50 |
| 10 µM 5-HT | 84 | 81 | 25 | 1.60 | 30 | 0.75 |
| 100 µM 5-HT | 91 | 72 | 67 | 68 | 48 | 67 |

Example 7

Effect of Serotonin on the Survival of Mouse RBCs

Figure 12:
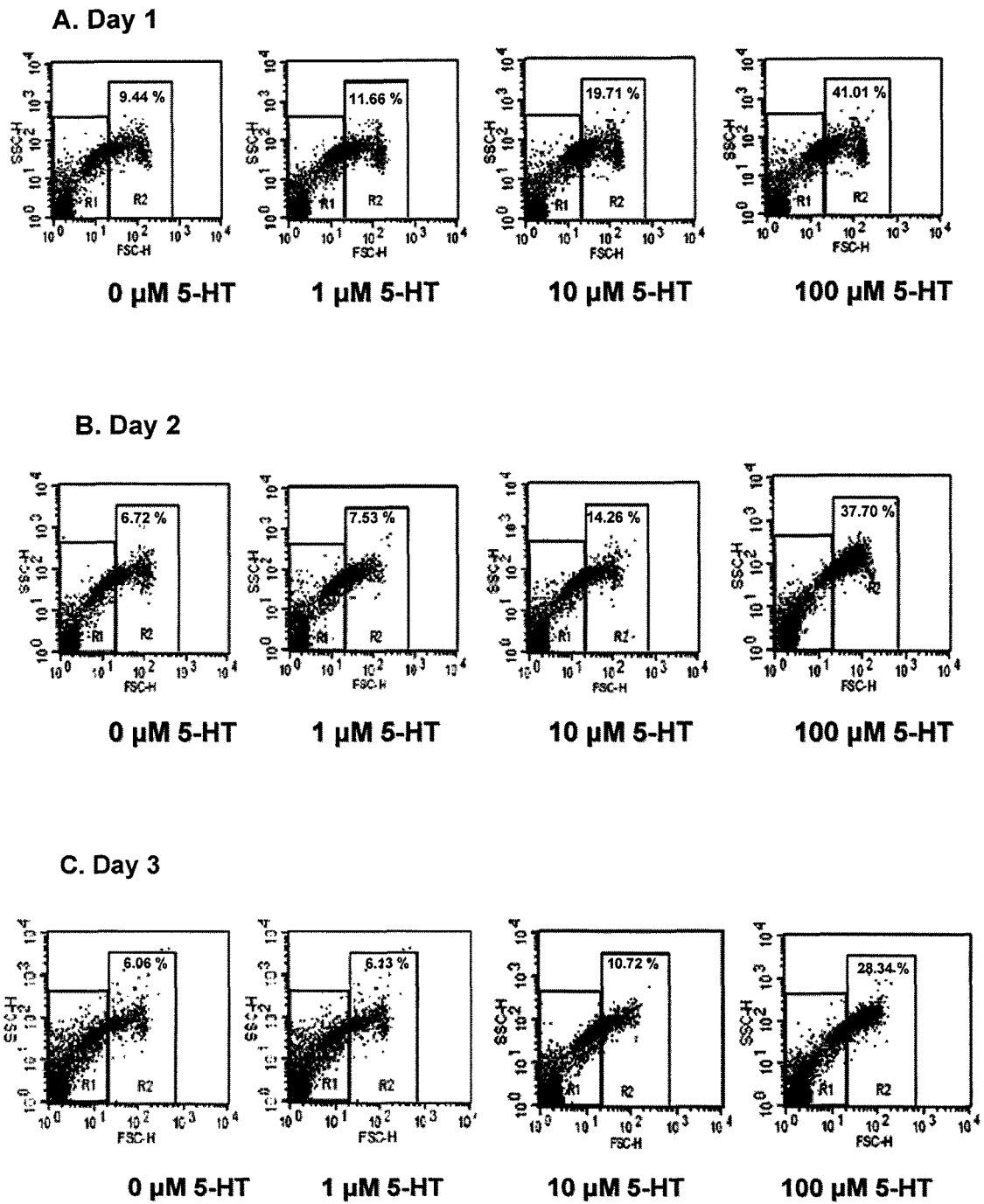
FIG. 12 shows the effect of 5-HT on the survival of mouse RBCs. Mouse RBCs were cultured at 37° C. for the indicated periods of time, in the presence of increasing concentrations of 5-HT (0-100 μM). Cell viability was assessed by flow cytometry at day 1 (A), day 2 (B), day 3 (C), day 5 (D) and day 7 (E), and the percentage of viable cells (% of cells in R2) is indicated.
Figure 12:
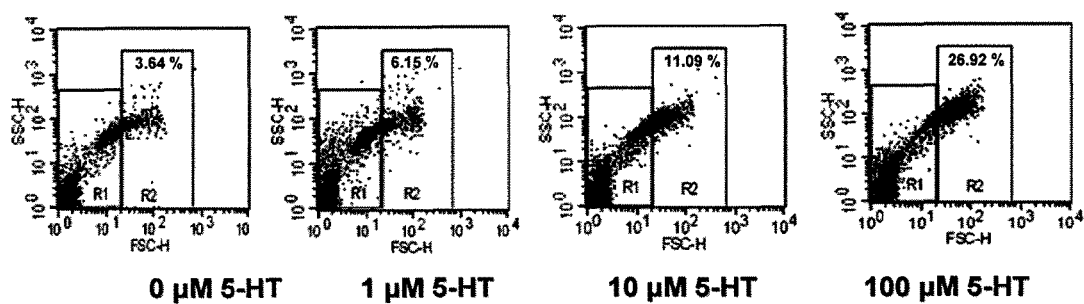
Figure 12:
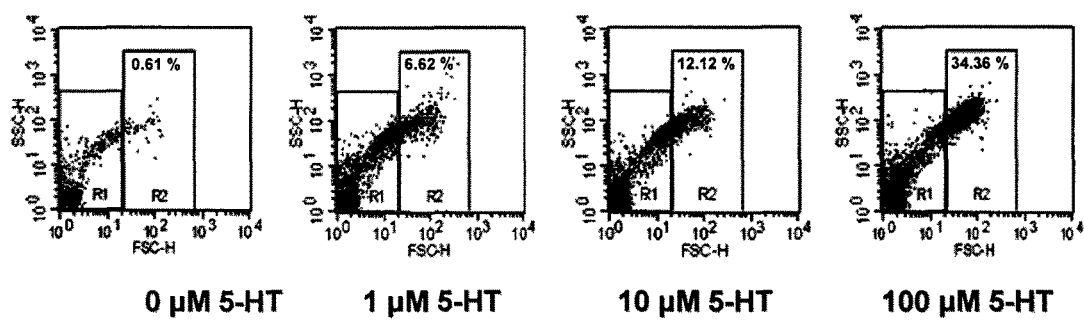

Having shown that serotonin has a protecting effect on human RBCs, it was next investigated whether serotonin also mediates its protecting effects on RBCs from another species, namely mouse RBCs. The data depicted in FIG. 12A-E show that the proportion of viable mouse RBCs is higher in the presence of 5-HT,. For example, the proportion of viable cells at day 7 is about 34% in the presence of 100 µM 5-HT, as compared to about 0.6% in 5-HT-free cultures (FIG. 12E). These results thus demonstrate that the protecting effect of 5-HT is not limited to human RBCs.

Example 8

Effect of Indole-comprising Compounds on RBC Survival

Figure 13:
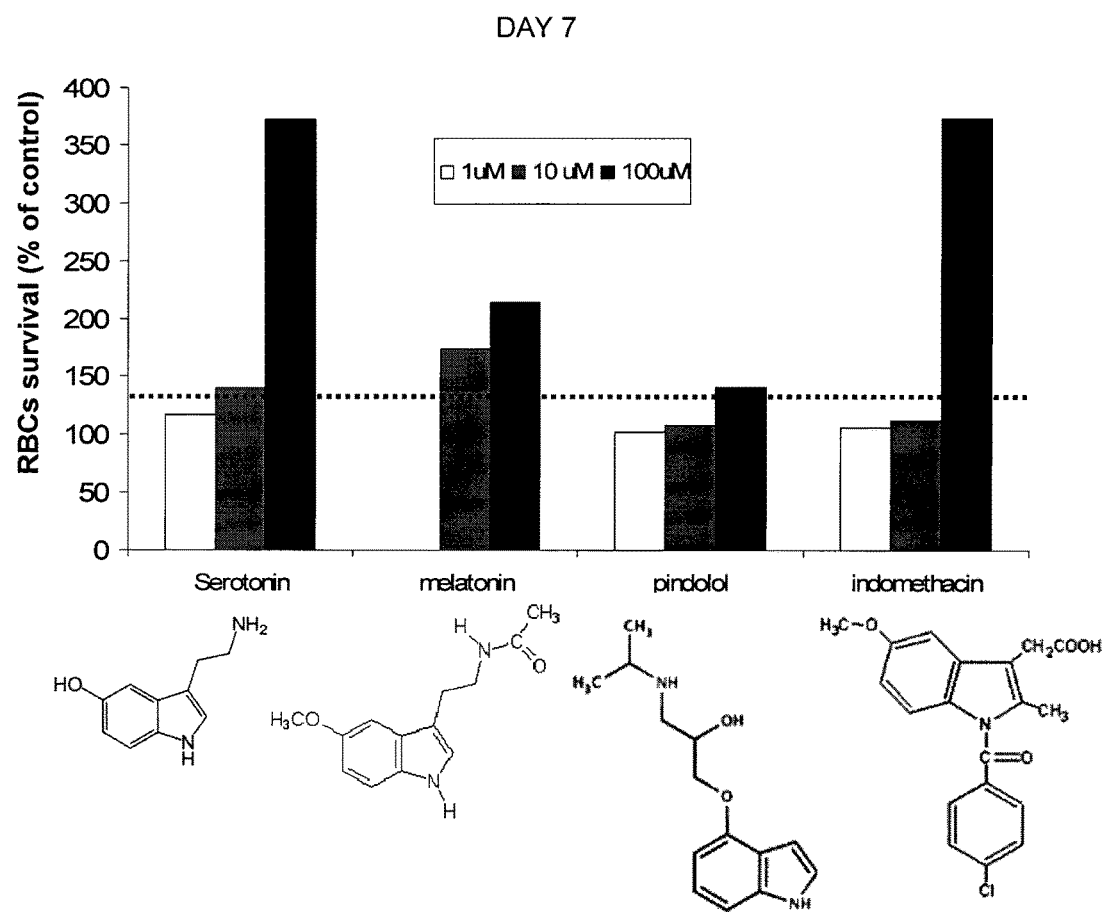
FIG. 13 shows the effect of various indole-comprising compounds (serotonin, melatonin, pindolol and indomethacin) on RBC survival. RBCs were incubated for 7 days at 37° C. in the presence or absence of different concentrations of the indicated indole compounds (white bars =1 μM; grey bars=10 μM; black bars:100 μM). As a control, RBCs were incubated in the presence of the appropriate buffer (without the compounds). RBCs survival in the presence of a given compound is expressed as the percentage of survival relative to the control.

The protecting effect on RBCs of various compounds comprising an indole moiety was assessed. The results depicted in FIG. 13 show that RBCs cultured for 7 days at 37° C. in the presence of melatonin, pindolol or indomethacin show increased survival as compared to RBCs cultured in the presence of buffer only. Therefore, these results show that other compounds having structural similarity to serotonin (notably the presence of an indole moiety) have a protecting effect on RBCs.

Although the present invention has been described hereinabove by way of specific embodiments thereof, it can be modified, without departing from the spirit and nature of the subject invention as defined in the appended claims. In the claims, the word "comprising" is used as an open-ended term, substantially equivalent to the phrase "including, but not limited to". The singular forms "a", "an" and "the" include corresponding plural references unless the context clearly dictates otherwise.

What is claimed is:

1. A blood or blood product storage kit comprising (a) a bag for ex vivo blood or blood product storage and (b) a conservation solution comprising from 10 µM to 200 µM of serotonin.

2. The storage kit of claim 1, wherein said conservation solution comprises citrate, mannitol, phosphate, dextrose, adenine, sodium chloride, or any combination thereof.

3. The storage kit of claim 2, wherein said conservation solution comprises citrate, mannitol, phosphate, dextrose, adenine and sodium chloride.

4. A method for preserving integrity of a blood sample or a blood product sample and/or preventing blood cell death in a blood sample or a blood product sample comprising storing said blood sample or a blood product sample in a blood or blood product storage kit comprising (a) a bag for ex vivo blood or blood product storage and (b) a conservation solution comprising from 10 µM to 200 µM of serotonin.

5. The method of claim 4, wherein said conservation solution comprises citrate, mannitol, phosphate, dextrose, adenine, sodium chloride, or any combination thereof.

6. The method of claim 5, wherein said conservation solution comprises citrate, mannitol, phosphate, dextrose, adenine and sodium chloride.

\* \* \* \* \*